US009339488B2

(12) United States Patent
Xu et al.

(10) Patent No.: US 9,339,488 B2
(45) Date of Patent: May 17, 2016

(54) ANTI-CERVICAL CANCER COMPOUND AND METHOD OF USE THEREOF

(71) Applicants: Hong Kong Baptist University, Hong Kong (HK); Shanghai University of Traditional Chinese Medicine, Shanghai (CN)

(72) Inventors: Hongxi Xu, Hong Kong (HK); Hong Zhang, Hong Kong (HK); Yuanzhi Lao, Hong Kong (HK); Xiaoyu Wang, Hong Kong (HK); Kaixian Chen, Hong Kong (HK); Dajian Yang, Hong Kong (HK); Shilin Chen, Hong Kong (HK); Chengyuan Lin, Hong Kong (HK); Zhaoxiang Bian, Hong Kong (HK); Aiping Lu, Hong Kong (HK); Albert Sun Chi Chan, Hong Kong (HK)

(73) Assignee: HONG KONG BAPTIST UNIVERSITY, Kowloon Tong, Kowloon (HK)

(*) Notice: Subject to any disclaimer, the term of this patent is extended or adjusted under 35 U.S.C. 154(b) by 54 days.

(21) Appl. No.: 14/449,132

(22) Filed: Jul. 31, 2014

(65) Prior Publication Data
US 2015/0038569 A1 Feb. 5, 2015

Related U.S. Application Data

(60) Provisional application No. 61/861,497, filed on Aug. 2, 2013.

(51) Int. Cl.
*A61K 31/352* (2006.01)
*A61K 36/062* (2006.01)

(52) U.S. Cl.
CPC ............. *A61K 31/352* (2013.01); *A61K 36/062* (2013.01)

(58) Field of Classification Search
CPC .................................................. A61K 31/352
See application file for complete search history.

(56) References Cited

FOREIGN PATENT DOCUMENTS

CN            102440985 A   *   5/2012

OTHER PUBLICATIONS

Lavaud, A., et al. "Paradoxical effects of polyphenolic compounds from Clusiaceae on angiogenesis." Biochemical Pharmacology. (2012), vol. 83, pp. 514-523.*
Chen, T., et al. "Tageting the S and G2 checkpoint to treat cancer." Drug Discovery. (Mar. 2012), vol. 17, No. 5/6, pp. 194-202.*
Pharmacorama.com. "Routes of drug administration." © 2006. Available from: < http://www.pharmacorama.com/en/Sections/Pharmacokinetics-5.php >.*
Xie, H., et al. "Effect of intratumoral administration on biodistribution of 64Cu-labeled nanoshells." International Journal of Nanomedicine. (2012), vol. 7, pp. 2227-2238.*
V. Reutrakul et al., "Cytotoxic and anti-HIV-1 caged xanthones from the resin and fruits of garcinia hanbury," Planta Med, 73: 33-40, 2007.
Q. B. Han et al., "Caged garcinia xanthones: development since 1937," Current Medicinal Chemistry, 16, 3775-3796, 2009.
Q. B. Han et al., "Cytotoxic Polyprenylated Xanthones from the Resin of Garcinia hanburyi," Chem Pharm Bull, 54(2), 265-267, 2006.
V. Rukachaisirikul et al., "Antibacterial caged-tetraprenylated xanthones from the stem bark of garcinia scortechinii," Planta Med, 71: 165-170, 2005.
S. W. Jang et al., "Gambogic amide, a selective agonist for TrkA receptor that possesses robust neurotrophic activity, prevents neuronal cell death," PNAS, vol. 104, No. 41, 16329-16334, (c) 2004.
P. D. Sampath et al., "Mitigation of mitochondrial dysfunction and regulation of eNOS expression during experimental myocardial necrosis by alpha-mangostin, a xanthonic derivative from garcinia mangostana," Drug and Chemical Toxicology, 32(4): 344-352, 2009.
S. Kasibhatla et al., "A role for transferrin receptor in triggering apoptosis when targeted with gambogic acid," PNAS, vol. 102, No. 34, 12095-12100, 2005.
M. K. Pandey et al., "Gambogic acid, a novel ligand for transferrin receptor, potentiates TNF-induced apoptosis through modulation of the nuclear factor-kB signaling pathway," Blood, 110: 3517-3525, 2007.
Y. Yang et al., "Differential apoptotic induction of gambogic acid, a novel anticancer natural product, on heptaoma cells and normal hepatocytes," Cancer Letters, 256, 259-266, 2007.
J. Yu et al., "Gambogic acid-induced G2/M phase cell-cycle arrest via disturbing CDK7-mediated phosphorylation of CDC2/p34 in human gastric carcinoma BGC-823 cells," Carcinogenesis, vol. 28, No. 3, pp. 632-638, 2007.
D. Zhai et al., "Gambogic acid is an antagonist of antiapoptotic Bcl-2 family proteins," Mol Cancer Ther, 7:1639-1646, 2008.
Q. Li et al., "Gambogenic acid inhibits proliferation of A549 cells through apoptosis-inducing and cell cycle arresting," Biol Pharm Bull, 33(3), 415-420, 2010.
Q. Qi et al., "Anti-invasive effect of gambogic acid in MDA-MB-231 human breast carcinoma cells," Biochem Cell Biol, 86: 386-395, 2008.

(Continued)

*Primary Examiner* — Noble Jarrell
*Assistant Examiner* — John S Kenyon
(74) *Attorney, Agent, or Firm* — Ella Cheong Hong Kong; Sam T. Yip

(57) ABSTRACT

Cervical cancer is one of the most common malignancies and is associated with a dismal prognosis. The most common therapeutic option for cervical cancer consists of surgery in early stages, and chemotherapy or radiotherapy in more advanced stages of the disease. Although treatment options have increased for some patients, overall progress has been modest. This invention relates to a method for treating cancer comprising administering an anti-cancer compound. More particularly, the present invention relates to an anti-cervical-cancer compound for treating human cervical cancer and tumor.

4 Claims, 6 Drawing Sheets

(56) References Cited

OTHER PUBLICATIONS

T. Yi et al., "Gambogic acid inhibits angiogenesis and prostate tumor growth by suppressing vascular endothelial growth factor receptor 2 signaling," Cancer Res, 68: 1843-1850, 2008.

Wu et al., "Gambogic acid inhibits proliferation of human lung carcinoma SPC-A1 cells in vivo and in vitro and represses telomerase activity and telomerase reverse transcriptase mRNA expression in the cells," Biol. Pharm. Bull, 27 (11) 1769-1774, 2004.

Q. Guo et al., "Toxicoloogical studies of gambogic acid and its potential targets in experimental animals," Basic & Clinical Pharmacology & Toxicology, 99, 178-184, 2006.

Q. Qi et al., "Studies on the toxicity of gambogic acid in rats," Journal of Ethanopharmacology, 117, 433-438, 2008.

J. Merza et al., "Prenylated xanthones and tocotrienols from Garcinia virgata," Phytochemistry, 65, 2915-2920, 2004.

Y. J. Xu et al., "Griffipavixanthone, a Novel Cytotoxic Bixanthone from Garcinia griffithii and G. pavifolia," Tetrahedron Letters, 39, 9103-9106, 1998.

Reagan-Shaw, S., Nihal, M. and Ahmad N., "Dose translation from animal to human studies revisited", The FASEB Journal, Life Science Forum. 22. 659-661, 2007.

* cited by examiner

ANTI-CERVICAL CANCER COMPOUND AND METHOD OF USE THEREOF

CROSS-REFERENCE TO RELATED APPLICATION

The present application claims benefit from the U.S. provisional patent application Ser. No. 61/861,497 filed Aug. 2, 2013, and the disclosure of which is incorporated herein by reference in its entirety.

FIELD OF INVENTION

The present invention relates to a method for treating cancer using an anti-cancer compound. More particularly, said anti-cancer compound is an anti-cervical-cancer compound. The present invention has a specific application in treating human cervical cancer.

BACKGROUND OF INVENTION

Cervical cancer is one of the most common malignancies and is associated with a dismal prognosis. The most common therapeutic option for cervical cancer consists of surgery in early stages, and chemotherapy or radiotherapy in more advanced stages of the disease. Although treatment options have increased for some patients, overall progress has been modest. The mechanism of clinical antitumor drugs can mainly be summarized as a cancer cell DNA replication inhibition process that leads to apoptosis. There is a lack of in-depth system research in another important signal path, such as autophagy, for anti-cancer treatments.

*Garcinia* species (Family Guttiferae) are tropical evergreen trees and shrubs that are widely distributed in Southeastern Asia and their phytochemistry has been widely studied. Classic and caged xanthones have been isolated from various parts of these plants, and identified as their major bioactive components. Traditionally, *Garcinia* resin (called gamboge) has been used in folk and Chinese medicine to promote detoxification, treat inflammation and wounds. Furthermore, recently xanthones isolated from various *Garcinia* species also showed antibacterial, antioxidant, antiviral and neuroprotective effects.

Gambogic acid, a caged xanthone found at high concentrations in gamboge, has been involved in the injectable antitumor drug since the 1970s. In 2004, gambogic acid has been granted permission for testing in clinical trial as a wide spectrum antitumor drug. Gambogic acid and its derivatives are cytotoxic in many cancer cell lines by binding to the transferrin receptor and induction of $G_2$/M cell cycle arrest and mitochondrial and death receptor-mediated apoptosis. Gambogic acid also reduces invasion and angiogenesis, telomerase mRNA expression and activity and tumor volume in vivo. However, the antitumor effect of gambogic acid can induce toxicity to the liver and kidney, which limits its development into a clinically useful anticancer drug.

Due to the toxicity of gambogic acid and other existing cancer treatments, there is a need to develop new anti-cancer treatments that possess selective cytotoxicity to cancers with low toxicity.

Citation or identification of any reference in this section or any other section of this application shall not be construed as an admission that such reference is available as prior art for the present application.

SUMMARY OF INVENTION

The first objective of the present invention is to provide a method of treating cervical cancer or cervical tumor comprising administering to a subject in need thereof a therapeutically effective amount of a composition comprising a compound of Griffipavixanthone having a chemical structure of Formula I:

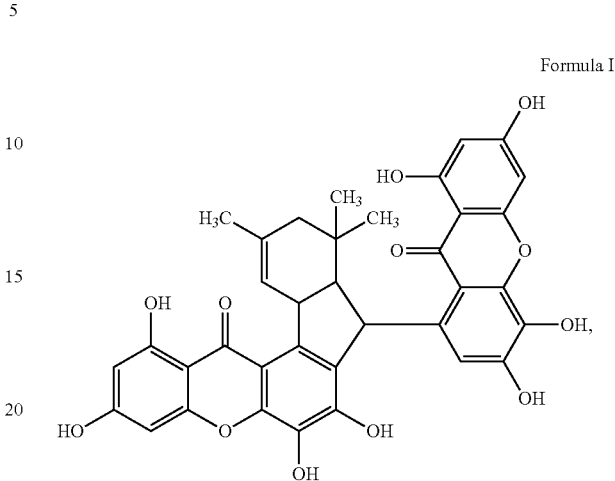

Formula I that induces autophagy.

In one embodiment, the therapeutically effective amount ranges from 3.2 ng to 6.4 ng per kg body weight of said subject per day of Griffipavixanthone and is administered at least once every two days for at least 18 days. In one embodiment, said composition is administered at least once a day for at least 18 days. Said subject in need thereof is a mammal. Said mammal includes, but is not limited to, human. In another embodiment, said composition is administered to the subject in need thereof through different routes which include, but are not limited to, oral, intraperitoneal, intravenous, intratumoral, and/or subcutaneous.

The second objective of the present invention is to provide a composition comprising a compound, Griffipavixanthone, having a chemical structure of Formula I:

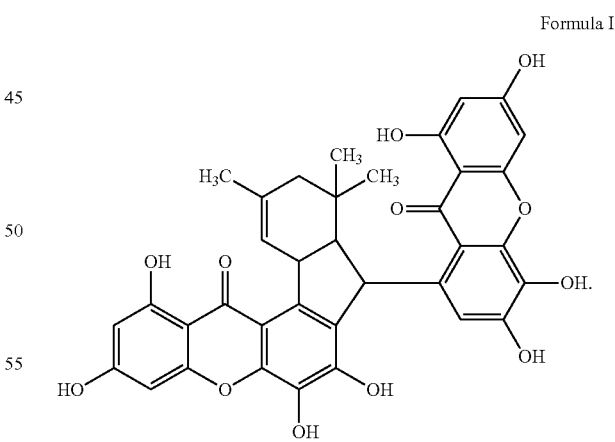

Formula I

Said composition is effectively in treating cervical cancer or cervical tumor in mammal. In one embodiment, the mammal includes, but is not limited to, human. In one embodiment, said composition comprises 3.2 ng to 6.4 ng per kg body weigh of the mammal of the compound of Formula I and is administered at least once every two days to be effective in treating cervical cancer or cervical tumor in said mammal. In another embodiment, said composition is administered at least once a day. In yet another embodiment, said composition is administered to said mammal at least once every two days or at least once a day for at least 18 days.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1:
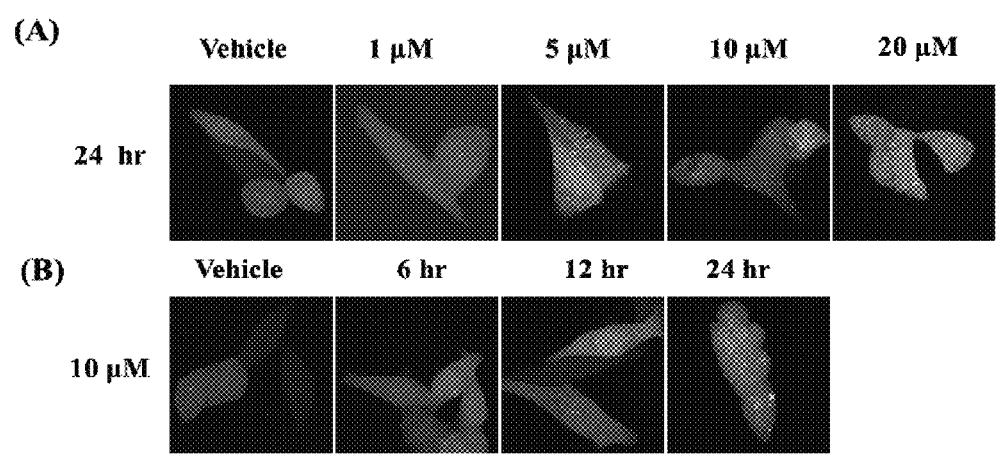
FIG. 1 shows fluorescence microscopy images of (A) HeLa-LC3-GFP cells treated with Griffipavixanthone (1-20 µM) for 24 hours and (B) Griffipavixanthone at the concentration of 10 µM (6, 12 and 24 hours)

The present invention is not to be limited in scope by any of the specific embodiments described herein. The following embodiments are presented for exemplification only.

Griffipavixanthone, a prenylatedxanthone, has been reported, in Xu, Y. J.; Gao, S. G.; Wu, X. H.; Tan, B. H. K., et al. Griffipavixanthone, a Novel Cytotoxic Bixanthone from *Garcinia griffithii* and *G. pavifolia*. Tetrahedron Letters. 1998, 39: 9103-9106, to have high in vitro cytotoxicity against three cell lines, notably leukemia cells, lung cancer cells and fibrosarcoma cells. However, there does not appear any study or publication documenting effectiveness of xanthone in inhibiting growth of cervical cancer or cervical tumor with low toxicity.

The present invention provides a compound, Griffipavixanthone, having potent and selective cytotoxicity to cervical cancer cells and tumors, with no or little toxicity, for use in treating cervical cancer or cervical tumor. The present invention discloses Griffipavixanthone significantly inhibits growth of cervical cancer cell HeLa in vitro and in vivo through autophagy. The present invention also shows that Griffipavixanthone is effective in inhibiting tumor growth in vivo.

The first aspect of the present invention, there is provided a method of treating cervical cancer or cervical tumor comprising administering to a subject in need thereof a therapeutically effective amount of a composition comprising a compound of Griffipavixanthone having a chemical structure of Formula I:

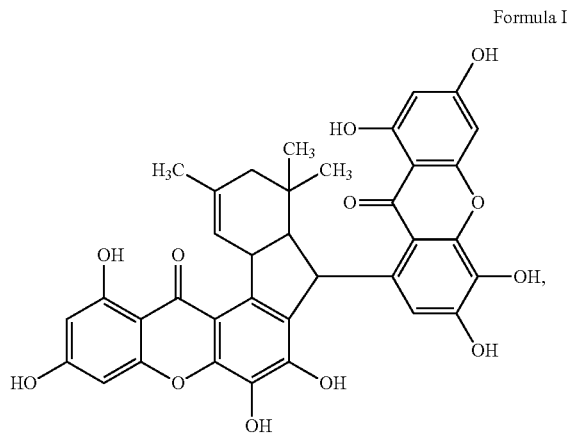 [SMILES: CC1=CC2c3c(c(O)c(O)c4oc5cc(O)cc(O)c5c(=O)c34)C(c3cc(O)c(O)c4oc5cc(O)cc(O)c5c(=O)c34)C2C(C)(C)C1]

Formula I that induces autophagy.

In one embodiment, the therapeutically effective amount ranges from 3.2 ng to 6.4 ng per kg body weight of said subject per day of Griffipavixanthone and is administered at least once every two days for at least 18 days. In one embodiment, said composition is administered at least once a day for at least 18 days. Said subject in need thereof is a mammal. Said mammal includes, but is not limited to, human. In another embodiment, said composition is administered to the subject in need thereof through different routes which include, but are not limited to, oral, intraperitoneal, intravenous, intratumoral, and/or subcutaneous.

The second aspect of the present invention, there is provided a composition comprising a compound, Griffipavixanthone, having a chemical structure of Formula I:

Formula I

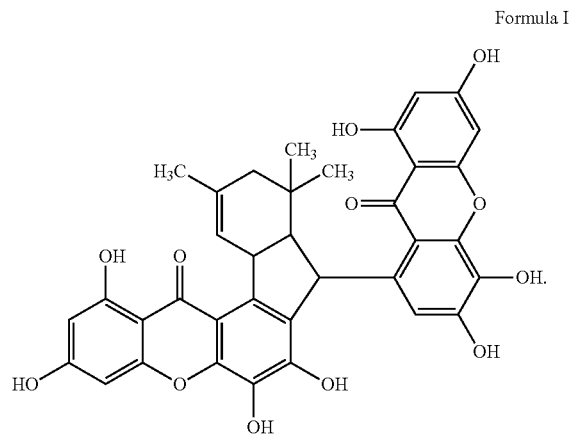 [SMILES: CC1=CC2c3c(c(O)c(O)c4oc5cc(O)cc(O)c5c(=O)c34)C(c3cc(O)c(O)c4oc5cc(O)cc(O)c5c(=O)c34)C2C(C)(C)C1]

Said composition is effectively in treating cervical cancer or cervical tumor in mammal. In one embodiment, the mammal includes, but is not limited to, human. In one embodiment, said composition comprises 3.2 ng to 6.4 ng per kg body weigh of the mammal of the compound of Formula I and is administered at least once every two days to be effective in treating cervical cancer or cervical tumor in said mammal. In another embodiment, said composition is administered at least once a day. In yet another embodiment, said composition is administered to said mammal at least once every two days or at least once a day for at least 18 days.

EXAMPLE 1

Extraction, Isolation and Identification

Air-dried and powdered twigs of the plant, G. esculenta (4 kg) are extracted with petroleum ether (5×20 L, for two days). Multiple extracts of G. esculenta are combined to give combined extract (i). The combined extracts (i) are evaporated to dryness under vacuum to gain the petroleum ether-soluble part (fraction I, 40 g). The remaining materials of combined extracts (i) are refluxed with 80% EtOH (v/v, 5×20 L). Multiple extracts of the remaining materials are combined to give combined extracts (ii). The combined extracts (ii) are evaporated to dryness under vacuum and the residue is suspended in H2O (5 L) and extracted with EtOAc (5×5 L) to obtain fractions II (50 g, the EtOAc-soluble part) and III (the remaining H2O part), respectively. The remaining materials of combined extracts (ii) are refluxed with distilled water (5×20 L) to gain the H2O-soluble part (fraction IV).

Fraction II is subjected to CC on MCI, eluted with 30%, 60%, 90%, 100% EtOH, and EtOAc, successively, to obtain subfractions IIA-IIE, respectively. Fractions IIB-IIC are shown to have the significant cytotoxic activities against human cancer cell lines (data not shown). Fraction IIC (14 g) is separated using a reversed-phase C18 silica gel column eluted with MeOH—H2O (60:40 to 100:0) as a gradient system to give nine subfractions (IIC1-IIC9). Fraction IIC6 is chromatographed on reversed-phase C18 silica gel eluted with MeOH—H2O in a gradient (45:55 to 100:0) to afford subfractions IIC6a-IIC6d. Fractions IIC6c is purified by Sephadex LH-20, eluted with MeOH to obtain Griffipavixanthone (150 mg).

EXAMPLE 2

In Vitro Studies of *Garcinia* Species on Human Cervical Cancer Cells (I) Cell Culture Human cervical cancer cell lines HeLa are maintained in DMEM (Invitrogen) supplemented with 10% newborn calf serum (Gibco, Life technologies Corporation, New Zealand), 1% penicillin/streptomycin (Invitrogen). Cells are maintained in a humidified atmosphere containing 5% $CO_2$ at 37° C.

(II) Assessment of Anti-Cancer Activity

Fluorescence Microscopy

Figure 2:
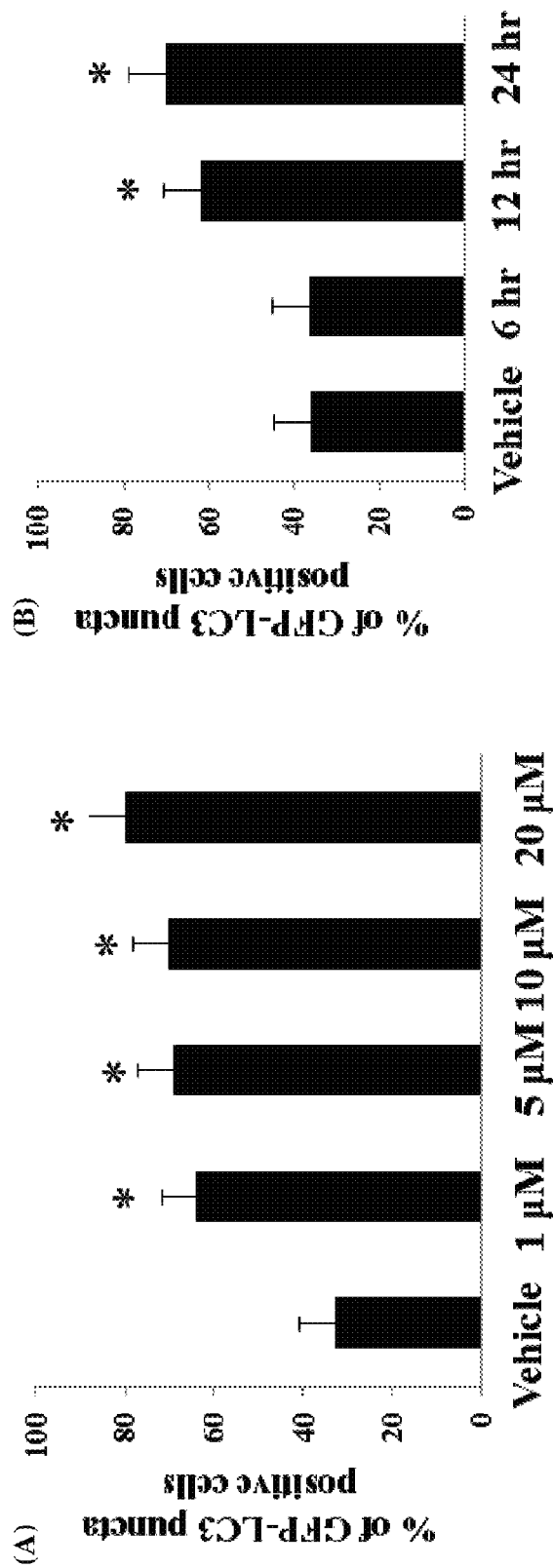
FIG. 2 is graphs showing percentage of GFP-LC3 positive cells. (A) HeLa-LC3-GFP cells are treated with DMSO (vehicle) or Griffipavixanthone (1-20 µM) for 24 hours. (B) HeLa-LC3-GFP cells are treated with 10 µM Griffipavixanthone for 6, 12 and 24 hours. Graphs show percentage of GFP-LC3 positive cells about Griffipavixanthone. *p<0.05, n=10

LC3, a known autophagy indicator, is used to show Griffipavixanthone's ability to induce autophagy in cancer cells and thus provide anti-cancer property. $1\times10^5$/ml HeLa LC3-GFP cells are seeded in a 35 mm×10 mm culture dish and preincubated for 24 hours before treatment with griffipavixanthone. HeLa LC3-GFP cells are treated with vehicle (control), 1 µM, 5 µM, 10 µM and 20 µM for 24 hours. After treatment of griffipavixanthone, the medium is removed from the dish and 4% methyl aldehyde with 0.3% triton-100 is added for fastening and permeation. The staining solution DAPI is added. Fluorescence of the bound dyes is analyzed using a laser scanning confocal microscope (FV10i, OlympusCorporation, Japan). FIG. 1 shows (A) LC3 puncta formation of HeLa LC3-GFP cells treat with vehicle (control), 1 µM, 5 µM, 10 µM and 20 µM for 24 hours and (B) with 10 µM griffipavixanthone for 6, 12 and 24 hours. FIG. 2 shows percentage of LC3-GFP positive signals increases along with an increases concentration (A) and time (B) of Griffipavixanthone treatment. It is shown that Griffipavixanthone increases GFP-LC3 puncta formation at concentration and time dependent manner. Griffipavixanthone induces autophagy in cervical cancer cells at concentration and time dependent manner.

Figure 3:
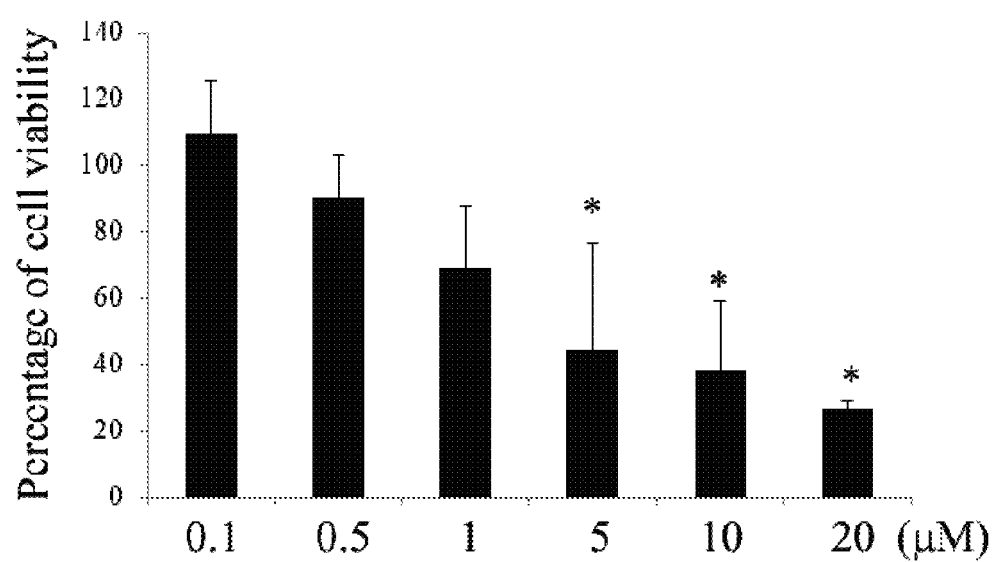
FIG. 3 shows the cytotoxic assay of Griffipavixanthone in HeLa cells. HeLa cells are treated with Griffipavixanthone (0.1-20 µM) for 72 hours

MTT Assay $4\times10^4$/ml HeLa cells are seeded in a 96-well plate and preincubated for 24 hours before treatment with Griffipavixanthone (0.1-20 µM). After 72 hours, 10 µl of MTT solution (5 mg/ml) (Sigma Chemical Company, St. Louis, Mo., USA) are added to each well for 4 hours. The resulting crystals are dissolved in DMSO. The controls are native cells treated with medium only. The spectrophotometric absorbance at 570 nm is measured using a microplate reader (Synergy HT, Bio-Tek Instruments Inc., Winooski, Vt., USA). The percentage cytotoxicity is calculated by the formula: Percentage cytotoxicity (cell death)=[1-(absorbance of experimental wells/absorbance of control wells)]×100%. As shown in FIG. 3, percentage of HeLa cells viability decreases as the concentration of Griffipavixanthone increases. Griffipavixanthone is shown to inhibit HeLa cell lines at concentration dependent manner by autophagy.

Figure 4:
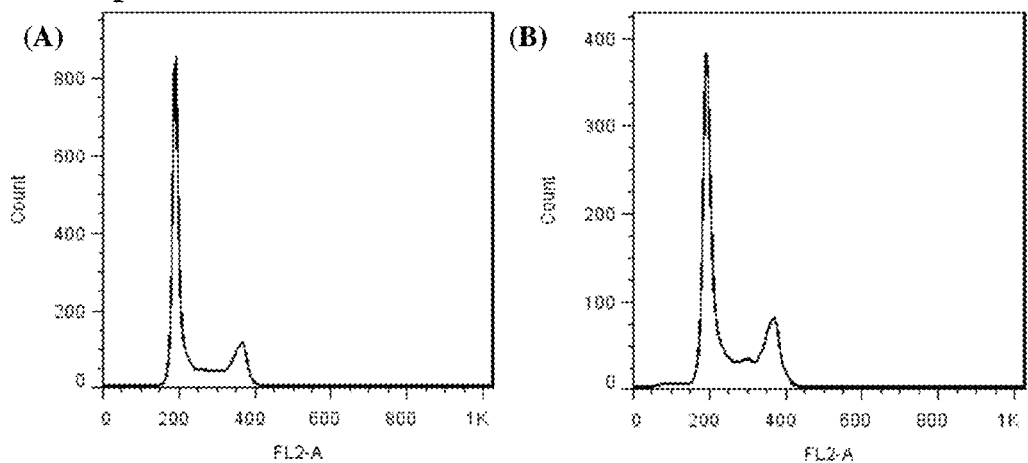
FIG. 4 shows histograms of FACS analysis of HeLa cells in DMEM treated with (A) 1 µM M Griffipavixanthone, (B) 10 µM Griffipavixanthone and HeLa cells in EBSS treated with (C) 1 µM Griffipavixanthone, (D) 10 µM Griffipavixanthone
Figure 4:
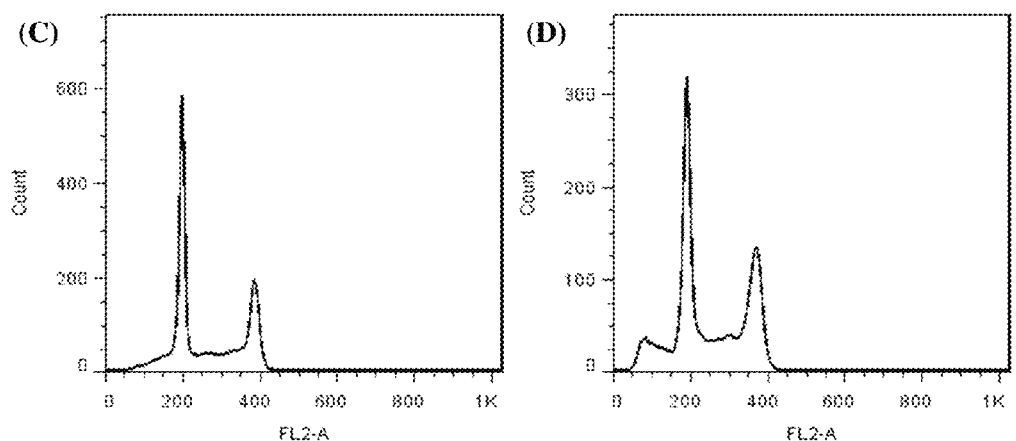

(III) FlowCytometer $3\times10^5$/ml HeLa cells are treated with Griffipavixanthone (1 and 10 µM) for 24 hours. Cells are trypsinized and fixed in ice-cold 100% methanol overnight at 4° C. Cells are washed, incubated with the staining solution (100 µg/ml RNase A and 20 µg/ml PI in Phosphate Buffer Saline (PBS) with 5% NBCS) for 60 minutes, and subjected to fluorescence activated cell sorting (FACS) analysis on a FACScan flowcytometer (BD PharMingen, USA). Data are analyzed using the FlowJo software. FIG. 4 shows FACS analysis of HeLa cells in DMEM treated with (A) 1 μM and (B) 10 μM Griffipavixanthone and HeLa cells in EBSS treated with (C) 1 μm and (D) 10 μM Griffipavixanthone. It is shown that Griffipavixanthone induces HeLa cell death significantly in serum-free medium at concentration dependent manner.

Figure 5:
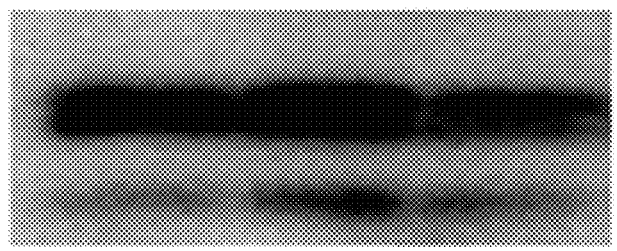
FIG. 5 shows the immunblot of LC3-I, LC3-II and p62 expression in HeLa cells treated with Griffipavixanthone at 0, 1 and 5 µM.
Figure 5:
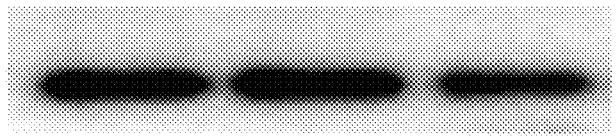
Figure 5:
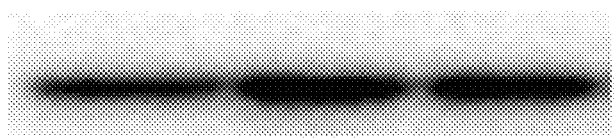

(IV) Western Blot Analysis $6 \times 10^5$/ml HeLa cells are treated with Griffipavixanthone (0, 1 and 5 μM) for 24 hours. Cells are collected and cleavaged by RIPA and PMSF. Proteins are extracted and separated by 12% gel SDS-PAGE, and then are transferred to PVDF. Membranes are blocked with 5% nonfat dry milk in TBST for 0.5 hour. They are incubated and exposed with the respective primary antibodies, testing the content change of protein. The primary antibodies used to detect proteins in autophagy pathway: LC3 (16, 18 kD), p62 (62 kD) and GAPDH (37 kD). FIG. 5 shows Griffipavixanthone increases autophagosome accumulation and induces autophagy.

EXAMPLES 3

Figure 6:
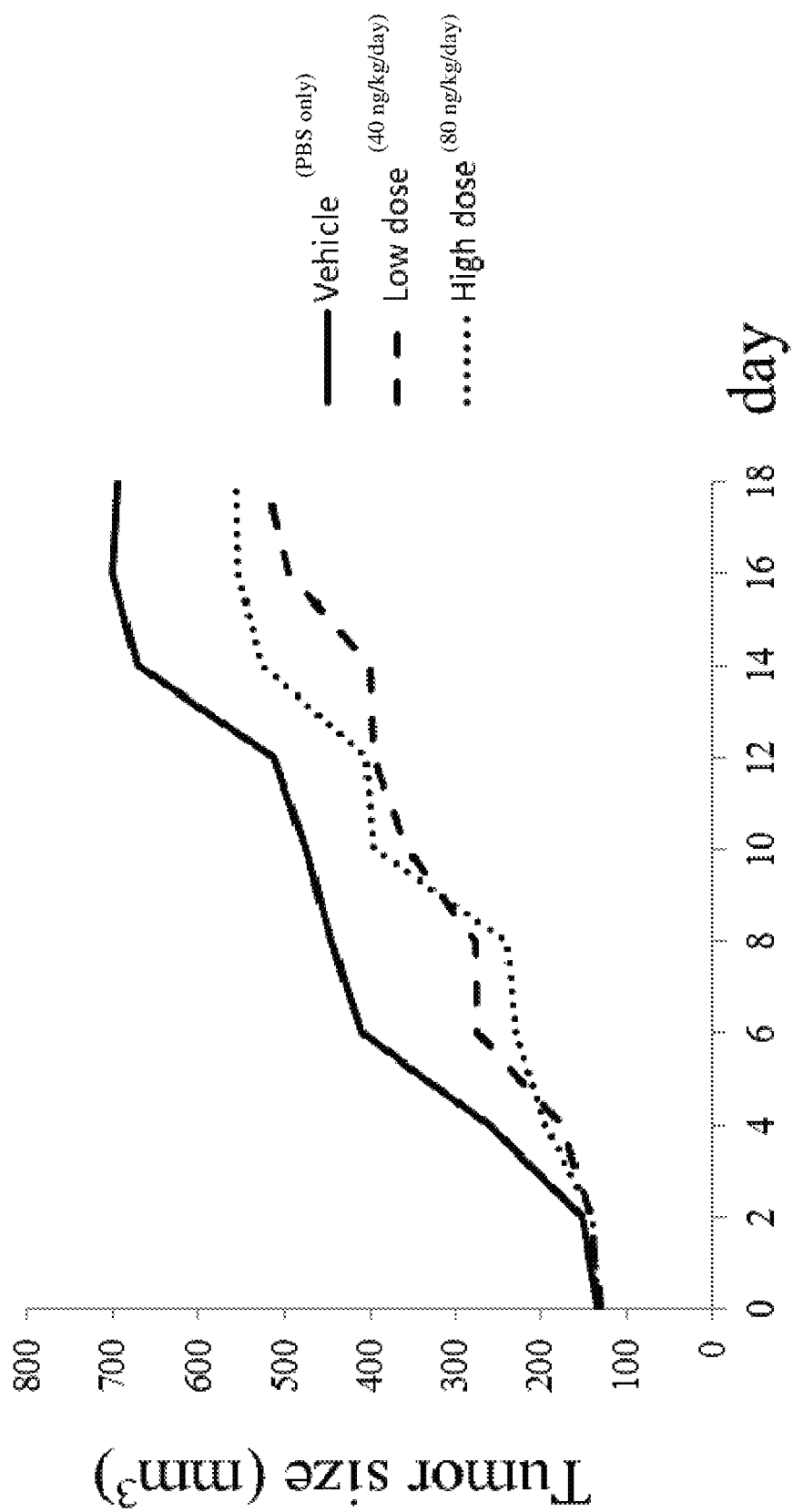
FIG. 6 shows the changes of tumor volume in HeLa Vehicle and Griffipavixanthone treatment (40 ng/kg/day and 80 ng/kg/day) groups.

In Vivo Studies of Griffipavixanthone on Inhibition of Tumor Growth in Xenograft Nude Mouse Model A total of $2 \times 10^6$ HeLa cells suspended in 100 μL of saline are inoculated s.c. into the right flank of 4-week-old male nude mice. Drug injections are made once the tumors reach an average volume of about 100 mm$^3$. Mice are divided randomly into two groups and subjected to intratumor injection of vehicle or Griffipavixanthone (40 ng/kg/day or 80 ng/kg/day) once every other day for 18 days. A total 2 μg/mouse and 4 μg/mouse are given to the two groups of mice in the 18 days treatment. Tumor volume is measured by caliper measurements ($V=L \times W^2/2$). For intratumor injection, Griffipavixanthone is prepared in 0.5% dimethyl sulfoxide, 0.5% tween 80, and 99% PBS. As shown in FIG. 6, the growth of tumor is inhibited by Griffipavixanthone injection. The dosage of administered Griffipavixanthone is translated to a human dosage of 3.2 ng/kg/day to 6.4 ng/kg/day with the equation: human equivalent dose=animal dose×animal Km/human Km, where mouse Km factor is 3 and human Km factor is 37 as disclosed in Reagan-Shaw, S., Nihal, M. and Ahmad N., "Dose translation from animal to human studies revisited", The FASEB Journal, Life Science Forum, disclosure of which is incorporated herein by reference in its entity.

Plant Material

*Garcinia esculenta* Y. H. Li twigs are collected in August 2010 in Nujiang, Yunnan Province, People's Republic of China. Plant material is identified by Prof. Yuanchuan Zhou, Yunnan University of Traditional Chinese Medicine. A voucher specimen (Herbarium No. 20100801) has been deposited at the Innovative Research Laboratory of TCM, Shanghai University of Traditional Chinese Medicine.

INDUSTRIAL APPLICABILITY

This invention provides an anti-cancer compound, Griffipavixanthone, and shows its potent and selective anti-cervical cancer effects. The present composition comprising Griffipavixanthone is useful for use as an anticancer drug, in particular an anti-cancer drug against cervical cancer, through inducing autophagy.

What is claimed is:

1. A method for treating cervical cancer and cervical tumors by administering to a subject in need thereof a composition comprising an effective amount of a compound having a chemical structure of

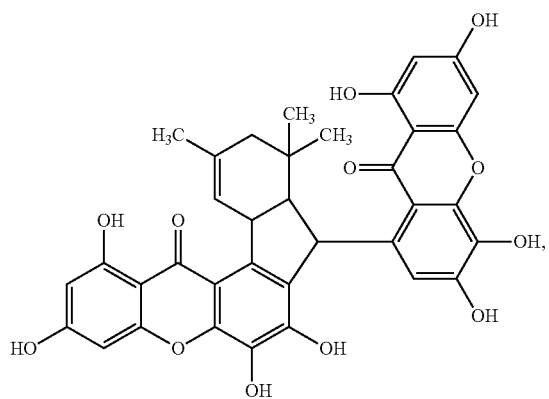 [SMILES: CC1=CC2c3c(c(O)c(O)c4oc5cc(O)cc(O)c5c(=O)c34)C(c3cc(O)c(O)c4oc5cc(O)cc(O)c5c(=O)c34)C2C(C)(C)C1]

wherein said composition is administered via intratumoral route at least once every two days and for at least 18 days.

2. The method according to claim 1 wherein the effective amount ranges from 3.2 ng/kg/day to 6.4 ng/kg/day of Griffipavixanthone.

3. The method according to claim 1 wherein said composition is administered to a human.

4. The method according to claim 1 wherein said intratumoral route is via intratumor injection.

* * * * *

UNITED STATES PATENT AND TRADEMARK OFFICE
CERTIFICATE OF CORRECTION

PATENT NO. : 9,339,488 B2  
APPLICATION NO. : 14/449132  
DATED : May 17, 2016  
INVENTOR(S) : Hongxi Xu et al.

Page 1 of 1

It is certified that error appears in the above-identified patent and that said Letters Patent is hereby corrected as shown below:

On the Title Page

Item (73) – Assignee, the correct Assignee's Name should be Hong Kong Baptist University and Shanghai University of Traditional Chinese Medicine.

Signed and Sealed this  
Fourteenth Day of April, 2020

Andrei Iancu  
*Director of the United States Patent and Trademark Office*